(12) United States Patent
Han et al.

(10) Patent No.: US 11,066,640 B2
(45) Date of Patent: Jul. 20, 2021

(54) *MICROBACTERIUM* SP. STRAIN AND METHOD FOR PRODUCING PSICOSE BY USING SAME (71) Applicant: SAMYANG CORPORATION, Seoul (KR)

(72) Inventors: Eun Jin Han, Seoul (KR); Sang-Hee Lee, Daegu (KR); Soun Gyu Kwon, Cheongju-si (KR); Bu-Soo Park, Daejeon (KR); Sin Hye Ahn, Goyang-si (KR); Chong Jin Park, Daejeon (KR); Kang Pyo Lee, Seoul (KR)

(73) Assignee: SAMYANG CORPORATION, Seoul (KR)

( * ) Notice: Subject to any disclaimer, the term of this patent is extended or adjusted under 35 U.S.C. 154(b) by 0 days.

(21) Appl. No.: 15/775,491

(22) PCT Filed: Dec. 1, 2016

(86) PCT No.: PCT/KR2016/014030
§ 371 (c)(1),
(2) Date: May 11, 2018

(87) PCT Pub. No.: WO2017/099418
PCT Pub. Date: Jun. 15, 2017

(65) Prior Publication Data
US 2020/0399721 A1    Dec. 24, 2020

(30) Foreign Application Priority Data
Dec. 7, 2015  (KR) ......................... 10-2015-0173489

(51) Int. Cl.
*C12P 19/02* (2006.01)
*C12N 1/20* (2006.01)
*C12R 1/01* (2006.01)

(52) U.S. Cl.
CPC .............. *C12N 1/205* (2021.05); *C12N 1/20* (2013.01); *C12P 19/02* (2013.01); *C12R 2001/01* (2021.05)

(58) Field of Classification Search
None
See application file for complete search history.

(56) References Cited

U.S. PATENT DOCUMENTS

2020/0080072 A1* 3/2020 Lee .......................... C12N 9/90

FOREIGN PATENT DOCUMENTS

| CN | 101177672 | 5/2008 |
| CN | 102373230 | 3/2012 |
| CN | 102869783 | 1/2013 |
| CN | 103131721 | 6/2013 |
| CN | 104919045 | 9/2015 |
| EP | 2944691 | 11/2015 |
| KR | 10-0832339 | 5/2008 |
| KR | 10-2011-0035805 | 4/2011 |
| KR | 10-2014-0064651 | 5/2014 |
| KR | 10-1473918 | 12/2014 |
| WO | 2015-099246 | 7/2015 |
| WO | 2017-099418 | 6/2017 |

OTHER PUBLICATIONS

Hye-Jung Kim et al., "Characterization of an Agrobacterium tumefaciens D-psicose 3-epimerase that converts D-fructose to D-psicose", Applied and Environmental Microbiology, 2006, vol. 72, No. 2, p. 981-985.
Deok-Kun Oh et al., "D-Psicose production from D-fructose using an isolated strain, *Sinorhizobium* sp.", World Journal of Microbiology and Biotechnology, 2007, vol. 23, No. 4, p. 559-563, Sep. 7, 2006, Kluwer Academic Publishers, DO, XP019485249.
Hiromichi Itoh et al., "Purification and characterization of D-Tagatose 3-Epimerase from *Pseudomonas* sp. ST-24", Bioscience, Biotechnology, and Biochemistry, 1994, vol. 58, No. 12, p. 2168-2171.
Undine Behrendt et al., "Description of *Microbacterium foliorum* sp. nov. and *Microbacterium phyllosphaerae* sp. nov., isolated from the phyllosphere of grasses and the surface litter after mulching the sward, and reclassification of Aureobacterium resistens (Funke et al. 1998) as *Microbacterium resistens* comb. nov.", International Journal of Systematic and Evolutionary Microbiology, 2001, vol. 51, p. 1267-1276.
F. Qian et al., "Isolation and characterization of a xanthan-degrading *Microbacterium* sp. strain XT11 from garden soil", Journal of Applied Microbiology, Wiley-Blackwell Publishing LTD, GB, vol. 102, No. 5, May 1, 2007, p. 1362-1371, XP002712291.
EPO, extended European search report of 16873283.2 dated Jun. 27, 2019.
Anonymous: "D-tagatose 3-epimerase [Microbacterium foliorum]", NCBI Reference Sequence: KJL27133.1, Retrieved from the Internet: URL:https://www.ncbi.nlm.nih.gov/protein/KJL27133.1/ [retrieved on Jul. 9, 2020].
Hiromichi Itoh et al., "Purification and Characterization of D-Tagatose 3-Epimerase from *Pseudomonas* sp.ST-24", Bioscience, Biotechnology, and Biochemistry, 1994, p. 2168-2171.
Zhang et al., "Characterization of D-tagatose-3-epimerase from Rhodobacter sphaeroides that converts D-fructose into D-psicose", Biotechnol Lett, vol. 31., p. 857-862, Feb. 2009.
NCBI, GenBank accession No. KJL27133.1, Mar. 19, 2015.
Ikuko Tsukamoto et al. "Intestinal absorption, organ distribution, and urinary excretion of the rare sugar D-psicose", Drug Design, Development and Therapy, vol. 8, p. 1955-1964, Oct. 2014.
Kwak, Ji Yean, "Temporal permission of standard and requirement on Microbacterium Foliorum SYC327B-MF(No. 2016-5)", National Institute of Food and Drug Safety Evaluation, Jul. 7, 2016.
Erika Corretto et al., "Draft Genome Sequences of 10 *Microbacterium* spp., with Emphasis on Heavy Metal—Contaminated Environments", Genome Announcements, vol. 3 Issue 3 e00432-15, May/Jun. 2015.
Mu Wanmeng et al., "Progress in Researches on D-tagatose 3-epimerase Family Proteins", Food and Fermentation Industries.2007;33(9)127-131.
Wei Bai et al., "Bioconversion of D-fructose to D-allose by novel isomerases", Chinese Journal of Biotechnology, 28(4): 457-465, Apr. 25, 2012.

* cited by examiner

*Primary Examiner* — Hope A Robinson
(74) *Attorney, Agent, or Firm* — Lex IP Meister, PLLC (57) ABSTRACT

The present invention relates to a newly isolated bacterium belonging to the genus *Microbacterium*, a composition for producing psicose comprising the strain, and a method for producing psicose using the same.

14 Claims, 4 Drawing Sheets
Specification includes a Sequence Listing.

SEQUENCE LISTING

```
<160> NUMBER OF SEQ ID NOS: 1

<210> SEQ ID NO 1
<211> LENGTH: 1466
<212> TYPE: DNA
<213> ORGANISM: Unknown
<220> FEATURE:
<223> OTHER INFORMATION: 16s rDNA

<400> SEQUENCE: 1
gatgaacgct ggcggcgtgc ttaacacatg caagtcgaac ggtgaacacg gagcttgctc      60
tgtgggatca gtggcgaacg ggtgagtaac acgtgagcaa cctacccctg actctgggat     120
aagcgctgga aacggcgtct aatactggat acgagtggcg accgcatggt cagctactgg     180
aaagatttat tggttgggga tgggctcgcg gcctatcagc ttgttggtga ggtaatggct     240
caccaaggcg tcgacgggta gccggcctga gagggtgacc ggccacactg ggactgagac     300
acggcccaga ctcctacggg aggcagcagt ggggaatatt gcacaatggg cgcaagcctg     360
```

-continued

```
atgcagcaac gccgcgtgag ggatgacggc cttcgggttg taaacctctt ttagcaggga    420
agaagcgaaa gtgacggtac ctgcagaaaa agcgccggct aactacgtgc cagcagccgc    480
ggtaatacgt agggcgcaag cgttatccgg aattattggg cgtaaagagc tcgtaggcgg    540
tttgtcgcgt ctgctgtgaa atccggaggc tcaacctccg gcctgcagtg ggtacgggca    600
gactagagtg cggtagggga gattggaatt cctggtgtag cggtggaatg cgcagatatc    660
aggaggaaca ccgatggcga aggcagatct ctgggccgta actgacgctg aggagcgaaa    720
gggtggggag caaacaggct tagatacccct ggtagtccac cccgtaaacg ttgggaacta    780 gttgtgggt ccattccacg gattccgtga cgcagctaac gcattaagtt ccccgcctgg     840
ggagtacggc cgcaaggcta aaactcaaag gaattgacgg gacccgcac aagcggcgga     900 gcatgcggat taattcgatg caacgcgaag aaccttacca aggcttgaca tatacgagaa    960
cgggccagaa atggtcaact ctttggacac tcgtaaacag gtggtgcatg gttgtcgtca   1020
gctcgtgtcg tgagatgttg ggttaagtcc cgcaacgagc gcaaccctcg ttctatgttg   1080
ccagcacgta atggtgggaa ctcatgggat actgccgggg tcaactcgga ggaaggtggg   1140
gatgacgtca aatcatcatg cccttatgt cttgggcttc acgcatgcta caatggccgg    1200
tacaaagggc tgcaataccg cgaggtggag cgaatcccaa aaagccggtc ccagttcgga   1260
ttgaggtctg caactcgacc tcatgaagtc ggagtcgcta gtaatcgcag atcagcaacg   1320
ctgcggtgaa tacgttcccg ggtcttgtac acaccgcccg tcaagtcatg aaagtcggta   1380
acacctgaag ccggtggcct aaccttgtg gagggagccg tcgaaggtgg gatcggtaat    1440
taggactaag tcgtaacaag gtaacc                                       1466
```

MICROBACTERIUM SP. STRAIN AND METHOD FOR PRODUCING PSICOSE BY USING SAME

CROSS-REFERENCE TO RELATED APPLICATIONS

This application claims the benefit of Korean Application No. 10-2015-0173489 filed on Dec. 7, 2015 with the Korean Intellectual Property Office, the entire disclosures of which are hereby incorporated by reference.

TECHNICAL FIELD

The present invention relates to a bacterium belonging to the genus *Microbacterium*, a composition for producing psicose comprising the bacterium, and a method for producing psicose using the same.

BACKGROUND ART

Generally, psicose is an epimer of no. 3 carbon of fructose (D-fructose). It has the sweetness degree corresponding to 70% compared to fructose, but it is hardly metabolized at the internal absorption in body unlike the fructose and it has a function to inhibit absorption of glucose and inhibit blood glucose. Therefore, it can be used for food and drink for diabetes patients or food and drink for guarding a body, and it can be used for various foods like health food, etc., because it has a function to inhibit an activity of enzyme involved in lipid synthesis in liver and thus it has a function to control blood sugar, prevent a cavity, and inhibit fat synthesis in liver, such as inhibiting accumulation of abdominal fat.

Sugar alcohols largely used as a sweetener substituted for sugar have side effects like causing diarrhea when absorbed over certain amount, etc., but psicose does not have a known side effect. Therefore, the psicose has been attracted as a diet sweetener, but the development of technology for effectively preparing the psicose is required to apply it into the food industry, as it belongs to a rare sugar which is a monosaccharide present in nature extremely rarely.

The conventional method for preparing the psicose is to prepare it mainly passing through chemical synthesis process like a chemical method of producing the psicose from a fructose using a catalytic action of molybdic acid ion. However, the chemical synthesis has a problem in that the psicose is present in a very small amount in a syrup treatment process or glucose isomerization process and it is costly and it produces a byproduct.

To solve such a problem, a biological method for preparing the psicose by an enzymatic reaction with a fructose as a substrate, such as producing the psicose from the fructose by psicose epimerase derived from *Agrobacterium tumefaciens* has been researched.

However, according to the conventional enzymatic method by using the enzyme with known function, the enzymes producing the psicose exhibit the optimum under the pH of alkaline condition, but the reaction under the alkaline condition induces non-specific reaction and browning of sugar, and therefore, it is not appropriate for industrialization. In addition, the conventional enzymes have a problem in that the yield of psicose production applied for industrialization is low and the manufacturing cost is increased as they have decreased stability or slow reaction rate at the high temperature. Thus, a method for producing a psicose with high yield under temperature and pH conditions proper for industrialization without producing a byproduct has been required.

DISCLOSURE

Technical Problem

One embodiment of the present invention provides a novel *Microbacterium* genus having a psicose conversion activity to produce a psicose from a fructose.

Another embodiment of the present invention provides a composition for producing a psicose comprising the *Microbacterium* genus, a culture of the strain, a supernatant of culture of strain, an extract of culture of strain, and/or a lysate of the strain.

Other embodiment of the present invention provides a method for producing a psicose from a fructose using the *Microbacterium* genus.

Other embodiment of the present invention provides a method for isolating a *Microbacterium* genus to produce an enzyme which converts a fructose into psicose from food.

Technical Solution

A novel *Microbacterium* genus (for example, *Microbacterium foliorum*) having an excellent activity of converting a fructose to a psicose was isolated and identified, the conversion activity from the fructose to psicose was confirmed by using microbial cells of the strain, and whether the optimum temperature, the optimum pH and metal ion of microbial cell reaction for obtaining the high conversion activity of psicose were needed was confirmed, thereby establishing the condition for effective mass production of psicose, to complete the present invention.

One embodiment of the present invention provides a novel bacterium belonging to the genus *Microbacterium* of converting a fructose to psicose.

Other embodiment provides a method for producing a psicose from a fructose by using the strain of *Microbacterium* genus. In the preparation method, the optimum reaction condition of microbial cells for obtaining the high psicose conversion activity and the condition for mass production of psicose are proposed.

Hereinafter, the present invention will be described in more detail.

At first, a novel bacterium belonging to the genus *Microbacterium* is provided. The bacterium belonging to the genus *Microbacterium* is a strain having excellent activity of converting a fructose to psicose, and it may be *Microbacterium foliorum*, *Microbacterium oxydans*, *Microbacterium maritypicum*, *Microbacterium liquefaciens*, *Microbacterium luteolum*, *Microbacterium ginsengiterrae*, *Microbacterium keratanolyticum*, *Microbacterium natoriense*, *Microbacterium lacticum*, *Microbacterium xylanilyticum*, *Microbacterium koreense*, *Microbacterium imperial* or *Microbacterium phyllosphaerae*, and preferably it may be one or higher kinds selected from the group consisting of *Microbacterium foliorum*, *Microbacterium oxydans*, and *Microbacterium phyllosphaerae*, and for example, it may be *Microbacterium foliorum* strain.

In one specific embodiment, the bacterium belonging to the genus *Microbacterium* may be *Microbacterium foliorum* SYG27B strain deposited as an accession number KCCM11774P.

The bacterium belonging to the genus *Microbacterium* is characterized by having excellent psicose conversion activity of converting a fructose to a psicose.

The psicose conversion activity is obtained as the bacterium belonging to the genus *Microbacterium* produces an enzyme converting a fructose to a psicose, and the *Microbacterium* genus may produce an enzyme having high psicose conversion activity, or may produce the psicose convertase in quantity, to exhibit excellent psicose conversion activity. Thus, the bacterium belonging to the genus *Microbacterium* may be usefully applied for preparation of psicose, and may enhance the yield of psicose production.

The psicose conversion activity may have the activity under the condition of temperature of 40° C. or higher, and for example, may exhibit the maximum activity under the condition of temperature of 50 to 80° C., 60 to 80° C., or 70 to 80° C., for example, 75° C.

In addition, the psicose conversion activity may have the high activity under the condition of pH 6.5 to 9.0, for example, pH 7.0 to 9.0, pH 7.5 to 9.0, pH 8.0 to 9.0 or 8.5 to 9.0. In particular, it may produce the psicose effectively in the neutral pH range of pH 7.0 to 8.0.

Thus, a composition for producing a psicose comprising one or higher kinds selected from the group consisting of a microbial cell of the bacterium belonging to the genus *Microbacterium* rain, a culture of the strain, an extract of the strain and a lysate of the strain is provided.

The culture comprises an enzyme produced from the bacterium belonging to the genus *Microbacterium* in and may comprise the strain or be a cell-free form of not comprising the strain.

The lysate means a lysate of crushing the bacterium belonging to the genus *Microbacterium* or a supernatant obtained by centrifuging the lysate, and comprises an enzyme produced from the bacterium belonging to the genus *Microbacterium*.

Herein, unless otherwise stated, the bacterium belonging to the genus *Microbacterium* used for preparation of psicose is used for meaning one or higher kinds selected from the group consisting of a microbial cell of the strain, a culture of the strain, and a lysate of the strain.

In addition, a method for preparing a psicose using the bacterium belonging to the genus *Microbacterium* is provided. The method for preparing a psicose comprises a step of reacting the strain of *Microbacterium* genus with a fructose.

In one specific embodiment, the step of reacting the strain of *Microbacterium* genus with a fructose may be performed by a step of culturing microbial cells of the strain of *Microbacterium* genus in a culture medium comprising a fructose.

In other specific embodiment, the step of reacting the bacterium belonging to the genus *Microbacterium* with a fructose may be performed by a step of contacting the strain (microbial cells, culture of strain, and/or lysate of strain) with a fructose, for example, a step of mixing the strain with a fructose or a step of contacting a fructose with a support in which the strain is immobilized. As such, by reacting the bacterium belonging to the genus *Microbacterium* with a fructose, a psicose may be produced from a fructose by converting the fructose into the psicose.

In the method for preparing a psicose, for effective production of psicose, the concentration of fructose used as a substrate may be 40 to 75% (w/v), 45 to 75% (w/v), for example, 50 to 75% (w/v), based on the total reactants. When the concentration of fructose is lower than the range, the economic becomes lower, and when it is higher than the range, the fructose is not dissolved well, and thus the concentration of fructose in the range is preferable. The fructose may be used as a liquid state dissolved in a buffer solution or water (for example, distilled water).

In the method for preparing a psicose, the reaction may be performed under the condition of temperature of 30° C. or higher, for example, 40° C. or higher. Since the browning of fructose as a substrate may be caused, when the temperature is 80° C. or higher, the reaction may be performed under the condition of 40 to 80° C., for example, 50 to 80° C., 60 to 80° C., or 70 to 80° C., for example, 75° C.

In addition, the reaction may be performed under the condition of pH 6.5 to 9.0, for example, pH 7.0 to 9.0, pH 7.5 to 9.0, pH 8.0 to 9.0 or 8.5 to 9.0, In particular, the effective production of psicose is possible even in the neutral pH range of pH 7.0 to 8.0.

In addition, in the method for preparing a psicose, the conversion rate of psicose is increased as the reaction time is longer. For example, it is preferable that the reaction time is 1 hour or higher, for example, 2 hours or higher, 3 hours or higher, 4 hours or higher, 5 hours or higher or 6 hours or higher. In addition, since the increasing rate of conversion rate of psicose is insignificant or rather decreased, when the reaction time is over 48 hours, it is preferable that the reaction time does not exceed 48 hours. Therefore, the reaction time may be 1 to 48 hours, 2 to 48 hours, 3 to 48 hours, 4 to 48 hours, 5 to 48 hours, or 6 to 48 hours, and it may be approximately 1 to 48 hours, 2 to 36 hours, 3 to 24 hours, 3 to 12 hours, or 3 to 6 hours, in consideration of industrial and economical aspects, but not limited thereto.

The condition is selected as the condition for maximizing the conversion efficiency from a fructose to a psicose.

In addition, in the method for preparing a psicose, the concentration of microbial cells of bacterium belonging to the genus *Microbacterium* may be 5 mg(dcw: dry cell weight)/ml or higher, for example, 5 to 100 mg(dcw)/ml, 10 to 90 mg(dcw)/ml, 20 to 80 mg(dcw)/ml, 30 to 70 mg(dcw)/ml, 40 to 60 mg(dcw)/ml, or 45 to 55 mg(dcw)/ml, based on the total reactants. When the concentration of microbial cells is less than the range, the psicose conversion activity is low or little, and when it exceeds the range, the total efficiency of psicose conversion reaction is lower as microbial cells are too many, and the range of the concentration of microbial cells is preferable.

Since the activation of an enzyme converting a fructose that the strain of *Microbacterium* genus produces into a psicose (for example, epimerase) may be controlled by a metal ion, in the production of psicose using the bacterium belonging to the genus *Microbacterium*, when a metal ion is added, the conversion efficiency from a fructose into a psicose, the production rate of psicose may be increased.

Therefore, the composition for preparing a psicose comprising the bacterium belonging to the genus *Microbacterium* may further comprise a metal ion. In addition, the method for preparing a psicose using the bacterium belonging to the genus *Microbacterium* may further comprise a step of adding a metal ion.

In one embodiment, the metal ion may be added in a culture medium in the culturing step, or the culturing step may be performed in a culture medium in which the metal ion is added. In another embodiment, the metal ion may be added to a fructose or added to the mixture of the bacterium belonging to the genus *Microbacterium* and fructose. In other embodiment, it may be added to a support in which the bacterium belonging to the genus *Microbacterium* is immobilized (before adding a fructose), or added to the mixture of support in which the bacterium belonging to the genus

*Microbacterium* is immobilized and fructose (after adding a fructose), or it may be added in a form of mixture with a fructose or respectively as adding a fructose.

The metal ion may be one or higher kinds selected from the group consisting of copper ion, manganese ion, calcium ion, magnesium ion, zinc ion, nickel ion, cobalt ion, iron ion, aluminum ion, etc. For example, the metal ion may be one or higher kinds selected from the group consisting of manganese ion, magnesium ion, nickel ion, cobalt ion, etc., and in one embodiment, the metal ion may be a manganese ion, a cobalt ion, or the mixture thereof.

When the manganese ion, cobalt ion, or mixture thereof is present as the metal ion, the psicose conversion activity may be increased 1.2 times, 1.3 times, 1.4 times, 1.5 times, 1.6 times, 1.7 times, 1.8 times, 1.9 times, 2.0 times, 2.1 times, 2.2 times, or 2.3 times, compared to the case without the metal ion, and for example, it may be increased 1.2 to 2.3 times.

In addition, when the added amount of metal ion is less than 0.5 mM, the effect of enhancing the psicose production yield is insignificant, and thus the added amount of metal ion may be 0.5 mM or higher. On the other hand, when the added amount of metal ion is over 5 mM, the effect is insignificant compared to the excess, and thus the added amount of metal ion may be 5 mM or less. For example, the added amount of metal ion may be in the range of 0.5 mM to 5 mM, 0.5 mM to 4 mM, 0.5 mM to 3 mM, for example, 0.5 mM to 2 mM.

The support may create an environment in which the activity of immobilized strain or enzyme produced from the strain can be maintained for a long period, and it may be all supports publicly known to be used for enzyme immobilization.

For example, soduim alginate may be used as the support. The sodium alginate is a polysaccharide abundantly present in a cell wall of seaweed, and is composed of mannuronic acid (β-D-mannuronic acid) and gluronic acid (α-L-gluronic acid), and forms beta-1,4 bond randomly in the aspect of content, and thereby the strain or enzyme is immobilized stably, and thus it is advantageous to exhibit the excellent psicose yield.

In one specific embodiment, for further enhancing the yield of psicose, a solution of sodium alginate of 1.5 to 4.0% (w/v) concentration (for example, sodium alginate aqueous solution), for example, a solution of sodium alginate of approximately 2.5% (w/v) concentration may be used for immobilization of strain. For example, after adding microbial cells of the strain, a culture comprising the enzyme produced by the strain, or a lysate of the strain to the sodium alginate aqueous solution in 1 to 2 volume times of microbial cells of strain, the culture comprising the enzyme produced by the strain or the lysate of the strain and mixing, by producing a bead by dropping the obtained mixed solution to approximately 0.2M calcium ion solution by using a syringe pump and a vacuum pump, the microbial cells of the strain, culture comprising the enzyme produced by the strain, or lysate of the strain may be immobilized in the sodium alginate support. The enzyme may be purified from the strain, strain culture or lysate of strain by methods such as common methods, for example, methods of dialysis, precipitation, adsorption, electrophoresis, affinity chromatography, ion exchange chromatography, etc.

The method for preparing a psicose proposed in the present invention can concert a fructose to a psicose by not using a buffer solution and using a microbial cell, and thus it has an advantage of producing a psicose with high yield by a simpler method.

Effect of the Invention

The present invention relates to a newly isolated bacterium belonging to the genus *Microbacterium*, a composition for producing psicose comprising the strain, and a method for producing psicose using the same, and since the bacterium belonging to the genus *Microbacterium* of the present invention has a stability in a useful range of pH, temperature and has an activity to produce a psicose from a fructose with high yield, it is expected that it would be widely used in functional sugar-related health food and pharmaceutical industries.

DETAILED DESCRIPTION OF THE EMBODIMENTS

The present invention will be described in more detail by the following examples. However, the following examples are desirable examples of the present invention, and the present invention is not limited thereto.

Example 1. Isolation of Food-Derived Microorganism Converting Fructose into Psicose To isolate a strain converting a fructose into a psicose, psicose-added Mineral salt broth ($KH_2PO_4$ 2.4 g/L, $K_2HPO_4$ 5.6 g/L, $(NH_4)_2SO_4$ 2.6 g/L, $MgSO_4 7H_2O$ 0.1 g/L, yeast extract 1 g/L) was used.

Food (for example, broccoli, ginseng, edible flower, etc.) was selected, and 1 g of each food was collected and added to MSP broth, and then cultured at 30° C. for 24 hours, thereby implementing enrichment. Then, 100 μL (microliter) of culture solution was collected and smeared on an agar medium, and then cultured at 30° C. until the colony was confirmed. Colonies having different shapes and sizes among colonies formed in the agar medium were selected and inoculated into MSP broth, and then shaking cultured at 30° C. for 24 hours and centrifuged to recover only microbial cells. The recovered microbial cells were put into 100 μL of 50 mM PIPES (piperazine-N, N'-bis(2-ethanesulfonic acid)) buffer solution (pH 7.0) and suspended, and lysated by using a ultrasonic processor (ColepParmer) to collect a lysate solution. After centrifuging the lysate solution by 12,000 rpm at 4° C. for 10 min, the supernatant was recovered and used as an enzyme solution (crude enzyme), and the enzyme solution was reacted at 30° C. for 12 hours with 10 mM fructose and psicose as substrates.

Whether the psicose was converted into the fructose in the reaction solution was confirmed by Thin Layer Chromatography (TLC) analysis. The thin layer chromatography analysis was performed by using a developing solvent of a stationary phase of silica gel (Silica gel 60F254 (Merck, Germany)) of width 20 cm, height 10 cm and a mobile phase mixing acetonitrile and water at the volume ratio of 85:15 and developing by 3 times for 10 min.

The strains in which a psicose was converted to a fructose confirmed by the TLC analysis were sorted and inoculated into 0.1% (w/v) psicose-added MS broth and shaking cultured at 30° C. for 24 hours, and after centrifugation, only microbial cells were recovered. The recovered microbial cells were washed with 0.85% (w/v) NaCl, and then suspended by putting 400 g/L fructose and 1 mM manganese ion-added 50 mM PIPES buffer solution (pH 7.0), and reacted at 70° C. for 1 hour.

Figure 1:
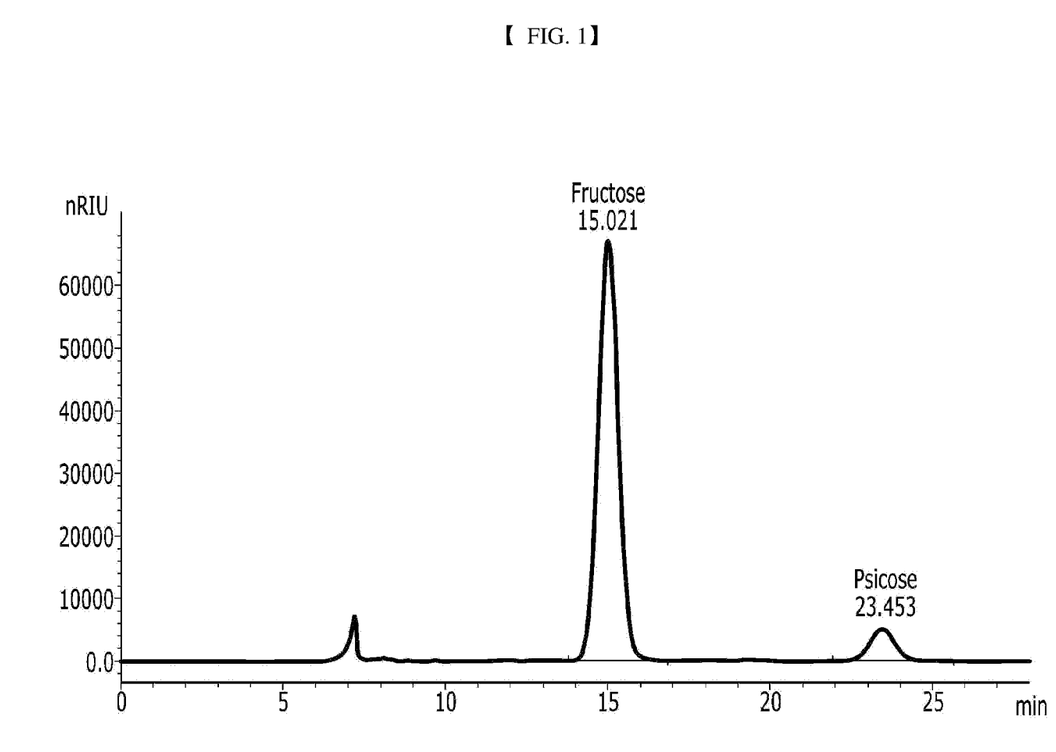
FIG. 1 is a graph showing a chromatogram confirming the psicose produced from the high concentration of fructose by High-Performance Liquid Chromatography (HPLC) in one example of the present invention.

Then, after recovering the supernatant by centrifuging the reaction results, High-Performance Liquid Chromatography (HPLC) analysis was carried out. The liquid chromatography analysis was performed by using RID (Refractive Index Detector, Agilent 1260 RID) of HPLC (Agilent, USA) equipped with Aminex HPX-87C column (BIO-RAD). Water was used as a mobile phase and the temperature was 80° C., and the flowing rate was 0.6 mL/min. The obtained result was shown in FIG. 1, and 1 kind of strain which produced psicose the most among 1500 kinds of strains was finally selected.

Example 2. Identification of Psicose Conversion Strain 2-1. Strain Identification The sequence of 16S ribosome RNA was confirmed to identify the strain isolated in Example 1. It was confirmed that the sequence (5'→3') of 16S ribosome RNA of isolated strain was same as SEQ ID NO: 1 and it was 99.5% homogeneous to *Microbacterium foliorum* DSM12966, and it was named *Microbacterium foliorum* SYG27B. The strain was deposited to Korean Culture Center of Microorganisms (Address: Yurim Building, 45, Hongjenae 2ga-gil, Seodaemun-gu, Seoul, Korea), which is an international depositary authority under the provisions of the Budapest Treaty, on Sep. 24, 2015 and the accession number KCCM11774P was given.

2-2. Psicose Conversion Activity of Strains of Same Genus

The strains identified as a bacterium belonging to the genus *Microbacterium* by the sequence of 16S ribosome RNA among isolated strains showing the psicose conversion activity in Example 1 were 3 kinds (*M. foliorum, M. oxydans, M. phyllosphaerae*). Among them, *M. foliorum*, which was considered to be superior in the aspect of stability since it was known to be isolated from broccoli and *ginseng*, was selected and the following experiments were carried out.

Example 3. Establishment of Optimum Condition Using Microbial Reaction of the Strain For the isolated strains, microbial cells and a substrate were reacted under various conditions of pH, temperature and metal ion, and the psicose conversion activities according to them were compared.

3-1. Analysis of Activity on Temperature Condition

Figure 2:
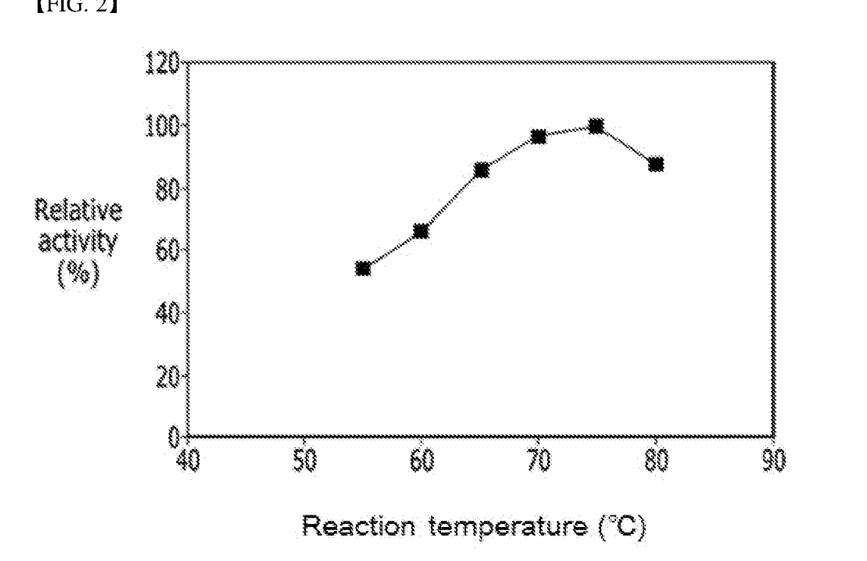
FIG. 2 is a graph showing relative activities of producing psicose of *Microbacterium foliorum* strain isolated in one example of the present invention according to the temperature.

To confirmed the optimum temperature for producing a psicose, the strain isolated in Example 1 in the concentration of microbial cells of 5 mg(dcw)/mL was reacted in 400 g/L fructose and 1 mM manganese metal ion-added 50 mM PIPES buffer solution (pH 7.0) for 1 hour as changing the temperature in the range of 55 to 80° C., and after the reaction was finished, the production of psicose was measured through HPLC analysis with the same method as Example 1, and the obtained result was shown in FIG. 2 and Table 1.

TABLE 1

| Reaction temperature (° C.) | Relative activity (%) |
|---|---|
| 55 | 54.2 |
| 60 | 66.1 |
| 65 | 85.8 |
| 70 | 96.7 |
| 75 | 100.0 |
| 80 | 87.7 |

As shown in FIG. 2 and Table 1, it was confirmed that the relative activity of *Microbacterium foliorum* SYG27B was increased as raising the reaction temperature by 75° C. and decreased at 80° C. In addition, the isolated strain exhibited the maximum activity at the temperature of 75° C.

3-2. Analysis of Activity on pH Condition

Figure 3:
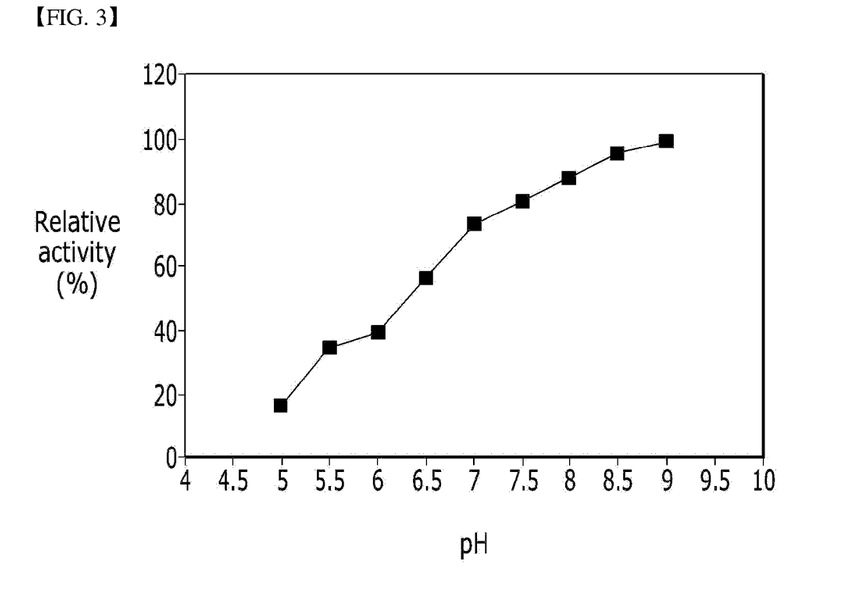
FIG. 3 is a graph showing relative activities of producing psicose of *Microbacterium foliorum* strain isolated in one example of the present invention according to pH.

To investigate the pH effect in the conversion reaction, the strain isolated in Example 1 in the concentration of microbial cells of 5 mg/mL was reacted by using 400 g/L fructose and 1 mM manganese metal ion-added McIlvaine (buffer solution prepared by adding 0.1 M citric acid and 0.2 M disodium hydrogen phosphate solutions in different amounts by pH) in the range of pH 5.0 to 9.0, respectively, at 70° C. for 1 hour, and after the reaction was finished, the production of psicose was measured through HPLC analysis with the same method as Example 1, and the obtained result was shown in FIG. 3 and Table 2.

TABLE 2

| pH | Relative activity (%) |
|---|---|
| 5.0 | 24.6 |
| 5.5 | 36.0 |
| 6.0 | 39.6 |
| 6.5 | 60.8 |
| 7.0 | 75.9 |
| 7.5 | 81.2 |
| 8.0 | 91.8 |
| 8.5 | 93.9 |
| 9.0 | 100.0 |

As shown in FIG. 3 and Table 2, it was confirmed that *Microbacterium foliorum* SYG27B which was the isolated strain obtained in Example 1 showed the high activity in the range of pH 6.5 to 9.0, and in particular, the effective production of psicose was possible even in the neutral pH range of pH 7.0 to 8.0.

3-3. Analysis of Activity on Metal Ion

Figure 4:
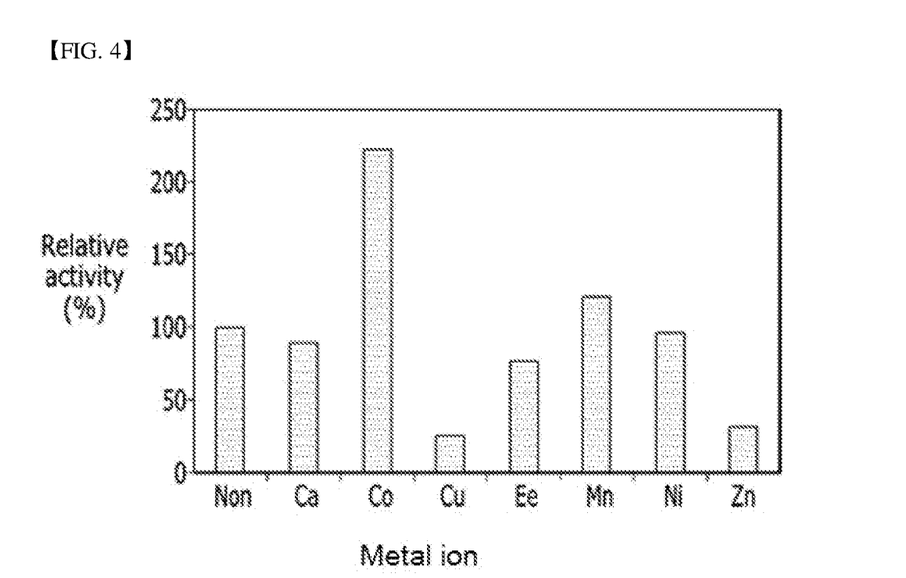
FIG. 4 is a graph showing relative activities of producing psicose of *Microbacterium foliorum* strain isolated in one example of the present invention according to the metal ion kind.

To confirm the needs of metal ion, using 400 g/L fructose as a substrate, and using the concentration of microbial cells isolated in Example 1 of 5 mg/mL, 70° C., and 1 mM metal ion ($CaCl_2$, $CoCl_2$, $CuCl_2$, $FeSO_4$, $MnCl_2$, $NiSO_4$, $ZnSO_4$) solution dissolved in 50 mM PIPES buffer solution (pH 7.0), respectively, it was reacted for 1 hour and after the reaction was finished, the production of psicose was measured through HPLC analysis with the same method as Example 1, and the obtained result was shown in FIG. 4 and Table 3.

TABLE 3

| Metal ion | Relative activity (%) |
|---|---|
| Non (control) | 100.0 |
| Ca | 90.1 |
| Co | 222.6 |
| Cu | 24.8 |
| Fe | 77.1 |
| Mn | 121.5 |
| Ni | 95.8 |
| Zn | 31.7 |

As shown in FIG. 4 and Table 3, compared to the control group in which no metal ion was added (Non), *Microbacterium foliorum* SYG27B obtained in Example 1 showed higher psicose conversion activity than the control group, when manganese (Mn) ion and cobalt (Co) ions were added.

Example 4. Condition for Mass Production of Psicose 4-1. Analysis of Temperature Stability of Microbial Cells To confirm the temperature stability of isolated strain, microbial cells isolated in Example 1 were suspended with 1 mM manganese ion-added 50 mM PIPES buffer solution (pH 7.0) and 50° C. of thermal shock for 36 hours was given. Then, after reacting them at 70° C. for 1 hour at the final fructose concentration of 400 g/L, and the concentration of microbial cells of 5 mg/mL, the psicose production was measured by time the thermal shock was given and the obtained result was shown in FIG. 5 and Table 4.

TABLE 4

| Time (hr) | Relative activity (%) |
|---|---|
| 0 | 100 |
| 2 | 93.4 |
| 4 | 77.8 |

TABLE 4-continued

| Time (hr) | Relative activity (%) |
|---|---|
| 8 | 65.1 |
| 12 | 59.7 |
| 24 | 53.1 |
| 36 | 46.1 |

Figure 5:
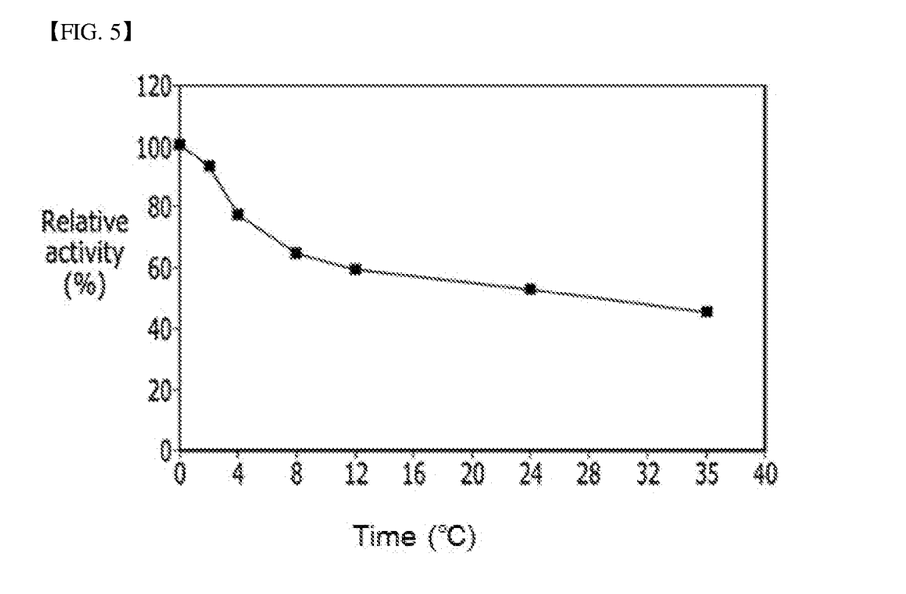
FIG. 5 is a graph showing the result of analysis of temperature stability of *Microbacterium foliorum* strain isolated in one example of the present invention at 50° C.

As shown in FIG. 5 and Table 4, it was shown that the half-life was approximately 28 hours, when the thermal shock was given for *Microbacterium foliorum* SYG27B obtained in Example 1 at 50° C., compared to the psicose conversion activity of *Microbacterium foliorum* SYG27B with no thermal shock.

4-2. Psicose Productivity

Under the established psicose mass production conditions, the maximum productivity according to the reaction time was confirmed. The activity by reaction time was confirmed under the conditions of the concentration of microbial cells of strain isolated in Example 1 of 20 mg/mL, the concentration of fructose of 400 g/L, the temperature of 70° C. and pH 7.0. The reaction was performed for 12 hours and the psicose productivity was confirmed by HPLC analysis in the 2 hour interval. The result was shown in FIG. 6 and Table 5.

TABLE 5

| Time (hr) | Relative activity (%) |
|---|---|
| 1 | 8.4 |
| 2 | 13.9 |
| 4 | 18.5 |
| 6 | 20.2 |
| 8 | 24.8 |
| 10 | 26.4 |
| 12 | 27.1 |
| 14 | 27.1 |

Figure 6:
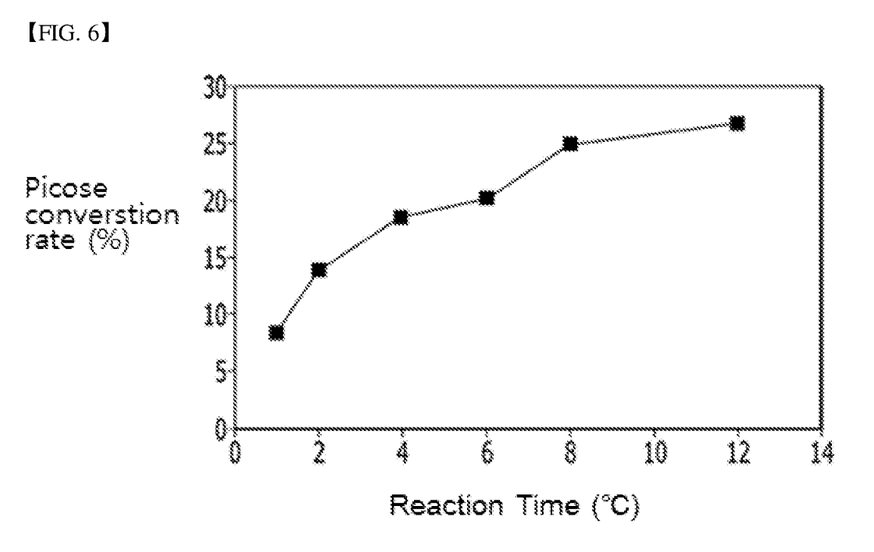
FIG. 6 is a graph showing the productivity of psicose at the high concentration substrate reaction.

As shown in FIG. 6 and Table 5, *Microbacterium foliorum* SYG27B showed the psicose conversion rate increased as the reaction time passed, and in particular, showed the maximum psicose conversion rate as approximately 27%, after the reaction at 70° C. for 12 hours, and then, the psicose productivity was confirmed as approximately 75 g/L.

The invention claimed is:

1. A method for producing psicose from fructose in the presence of manganese ion (Mn$^{2+}$), comprising:
contacting the fructose with a microbial cell of *Microbacterium foliorum* having psicose conversion activity to produce psicose from fructose, a culture of *Microbacterium foliorum*, a culture supernatant of *Microbacterium foliorum*, a culture extract of *Microbacterium foliorum*, and/or a lysate of *Microbacterium foliorum*, wherein the *Microbacterium foliorum* has an increased psicose conversion activity in the presence of manganese ion (Mn$^{2+}$) compared to absence of manganese ion.

2. The method for producing the psicose of claim 1, wherein the contacting comprises culturing the *Microbacterium foliorum* in a medium containing the fructose.

3. The method for producing the psicose of claim 1, wherein the contacting is performed by contacting the fructose to a support immobilized with a microbial cell of *Microbacterium foliorum*, a culture of *Microbacterium foliorum*, a culture supernatant of *Microbacterium foliorum*, a culture extract of *Microbacterium foliorum*, and/or a lysate of *Microbacterium foliorum*.

4. The method for producing the psicose of claim 1, wherein the method further comprises adding one or more kinds of metal ions selected from the group consisting of manganese and cobalt.

5. The method for producing the psicose of claim 1, wherein the method is performed by not using a buffer solution.

6. The method for producing the psicose of claim 1, wherein the fructose has a concentration of 40 to 75% (w/w).

7. The method for producing the psicose of claim 1, wherein the method is performed under the condition of pH 6.5 to 9.0 and 40 to 80° C.

8. The method for producing the psicose of claim 1, wherein the *Microbacterium foliorum* is deposited in Korean Culture Center of Microorganism under Accession Number KCCM11774P.

9. A composition for producing psicose from fructose, comprising a microbial cell of *Microbacterium foliorum* having psicose conversion activity to produce psicose from fructose, a culture of *Microbacterium foliorum*, a culture supernatant of *Microbacterium foliorum*, a culture extract of *Microbacterium foliorum*, and/or a lysate of *Microbacterium foliorum*, and
manganese ion (Mn$^{2+}$),
wherein the *Microbacterium foliorum* has an increased psicose conversion activity in the presence of manganese ion (Mn$^{2+}$), compared to absence of manganese ion.

10. The composition of claim 9, wherein the *Microbacterium foliorum* has psicose conversion activity at 40 to 80° C.

11. The composition of claim 9, wherein the *Microbacterium foliorum* has psicose conversion activity at pH 6.5 to 9.0.

12. The composition for producing the psicose of claim 9, wherein the *Microbacterium foliorum* has 1.2 to 2.3 times increased psicose conversion activity in the presence of one or more kinds of metal ions selected from the group consisting of manganese and cobalt compared to absence of the metal ion.

13. The composition for producing the psicose of claim 9, wherein the *Microbacterium foliorum* is deposited in Korean Culture Center of Microorganism under Accession Number KCCM11774P.

14. A *Microbacterium foliorum* deposited in Korean Culture Center of Microorganism under Accession Number KCCM11774P.

\* \* \* \* \*